(12) United States Patent
Szydlo-Moore

(10) Patent No.: US 7,110,095 B2
(45) Date of Patent: Sep. 19, 2006

(54) MULTIPLE ADAPTABLE 3-DIMENSIONAL ULTRA-HIGH SPEED SCANNING SYSTEM FOR ORGANIC AND INORGANIC SURFACE TOPOGRAPHY AND SPECTROMETRY

(75) Inventor: Joanna Szydlo-Moore, Everett, WA (US)

(73) Assignee: Joanna A Szydlo-Moore, Everett, WA (US)

( * ) Notice: Subject to any disclaimer, the term of this patent is extended or adjusted under 35 U.S.C. 154(b) by 218 days.

(21) Appl. No.: 10/638,650

(22) Filed: Aug. 11, 2003

(65) Prior Publication Data
US 2005/0036133 A1 Feb. 17, 2005

(51) Int. Cl.
*G01N 21/00* (2006.01)
(52) U.S. Cl. .......................... 356/73; 356/326
(58) Field of Classification Search ............. 356/73, 356/345, 450; 250/227.27, 227.19, 221, 250/340, 339.12, 339.09, 339.07
See application file for complete search history.

(56) References Cited

U.S. PATENT DOCUMENTS 6,015,969 A * 1/2000 Nathel et al. .......... 250/227.27
6,657,727 B1 * 12/2003 Izatt et al. ................. 356/450

OTHER PUBLICATIONS

J. Szydlo, et al., Air-Turbine Driven Low-Coherence Reflectometry at 28.6-kHz Scan Repetition Rate, 4 pages, Apr. 14, 1998.
J. Szydlo, et al., High-Speed Measurements in Optical Low-Coherence Refleftometry, 4 pages, Apr. 17, 1998.
J. Szydlo, et al, High Speed Depth Optical Scanner, 138 pages Lausanne, EPFL, Dec. 21, 2000.
ETH. Switzerland, Web Page; High Speed Optical Scanner, 1 page, 1/14/1003.

* cited by examiner

*Primary Examiner*—Michael P. Stafira

(57) ABSTRACT

A 3-dimensional ultra-high speed scanning system for organic and inorganic surface topography and spectrometry has a 3-dimensional head to scan an object to be analyzed. The scanning head is operatively associated with a path length variator which in turn is operatively connected to a single mode wavelength coupler. A light source and a photo detector are operatively connected to the wavelength coupler. A computer with software for data reduction and 3-dimensional representation are connected to both the light source and the photo detector to reveal scanning data of an object scanned by the scanning head. A spectrometer is alternately coupled to the photo detector.

30 Claims, 9 Drawing Sheets

US 7,110,095 B2

MULTIPLE ADAPTABLE 3-DIMENSIONAL ULTRA-HIGH SPEED SCANNING SYSTEM FOR ORGANIC AND INORGANIC SURFACE TOPOGRAPHY AND SPECTROMETRY

BACKGROUND OF THE INVENTION

Optical low clearance reflectometry (OLCR) methods is a classical optical method which can be used to measure distances to objects with high precision. The method is based on coherent cross-correlation of light reflected from the object being scanned. OLCR methodology has been based upon a transparent cube which is rotated at very high speeds. Some problems occurring include precise alignment, optical stability, vibrations and dynamic deformations due to high rotational speeds.

Among the greatest shortcomings of OLCR high speed methods is that they conventionally scan in a 1-D mode. While attempts have been made to theorize adapting OLCR to a 3-D mode to obtain 3-dimensional data, such 3-D technology has not been readily forthcoming.

Further, existing OLCR scanners are not flexible to enable optimum scan rate, depth and resolution for the subject the user desires to analyze.

It is therefore a principal object of this invention to provide a multiple adaptable 3-dimensional ultra-high speed scanning system for organic and inorganic surface topography and spectrometry which is adaptable to enable optimum scan rate, depth and resolution for the subject the user desires to analyze.

A further object of the invention is to provide a multiple adaptable 3-dimensional ultra-high speed scanning system for organic and inorganic surface topography and spectrometry which can be upgradeable with spectrometry to afford the user with a very flexible high sustained value device that is not limited to one application and analysis capability.

A still further object of this invention is to provide a multiple adaptable 3-dimensional ultra-high speed scanning system for organic and inorganic surface topography and spectrometry which couples ultra-high speed topography and spectrometry for simultaneous 3-dimensional analysis of the surface topography and chemical composition of subjects that are not necessarily stationary, but can be.

More specifically, it is an object of this invention to provide a multiple adaptable 3-dimensional ultra-high speed scanning system for organic and inorganic surface topography and spectrometry which is capable of detecting the presence, identity and quantity of micro particulates/contaminant imperfections on complex organic or inorganic surfaces.

These and other objects will be apparent to those skilled in the art.

SUMMARY OF THE INVENTION

A 3-dimensional ultra-high speed scanning system has a mobile 3-dimensional head to scan an object to be analyzed. The scanning head is operatively associated with a path length variator which in turn is operatively connected to a single mode wavelength coupler. A light source and a photo detector are operatively connected to the wavelength coupler. A computer with software for data reduction and 3-dimensional representation ideally 3-D color graphs of surface topography and chemical composition are connected to both the light source and the photo detector to reveal scanning data of an object scanned by the scanning head. A spectrometer is alternately coupled to the detector associated with the spectrometer is alternately coupled to the computer which is coupled to the scanning head.

DESCRIPTION OF THE PREFERRED EMBODIMENTS

This invention is an extension of Applicant's thesis entitled "High Speed Depth Optical Scanner" (2000). That thesis is herein incorporated by reference.

Figure 1:
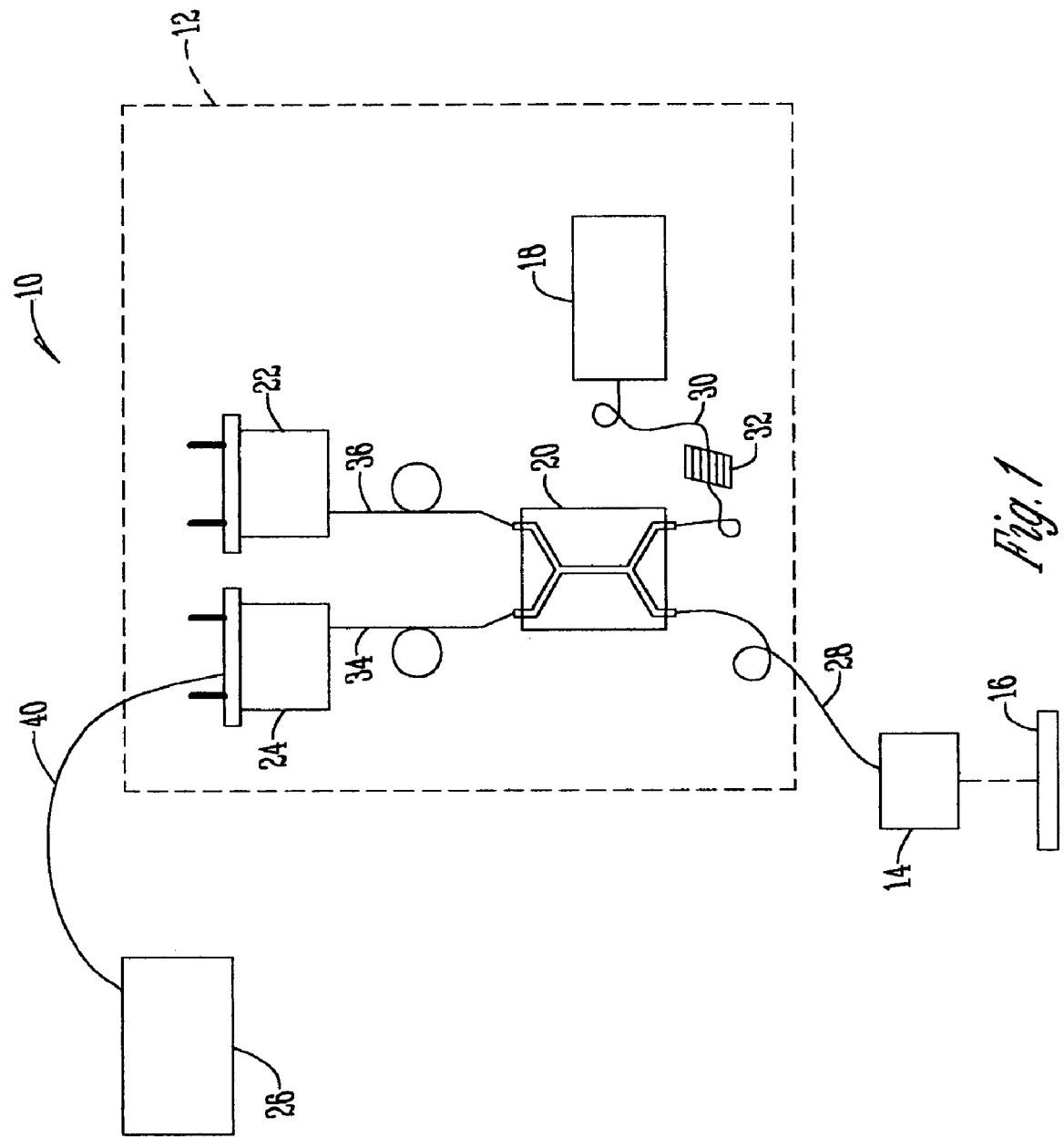
FIG. 1 is a schematic view of the topography of the system of this invention.

FIG. 1 shows a topography schematic view of the OLCR system 10. An enclosure 12 is provided to contain the principal parts of the system. The numeral 14 designates a mobile angular scanning head which is within a container lined with fire retardant non-reflective impact absorbing material, as is the enclosure 12. The numeral 16 in FIG. 1 designates the object being scanned.

A path length variator 18 is located within enclosure 12 as is a single mode wavelength coupler 20. Coupler 20 is preferably provided with 633 nm center wavelengths. Also, within enclosure 12 is a light source 22 and a photo detector 24. The light source is preferably provided by a laser photo-diode having up to the highest power available for inorganic subjects, and expendable, or deceased/perished organic subjects. For living organic substances the modular light source is exchanged with a light source of power that is limited to that which is deemed safe for the subject. The wavelength of the light source for either case is preferably between 400 and 1700 mm. The photo detector is preferably that which is most compatible with the performance of the system including the rotational speeds and light source, and safety of the subject. 6 $GH_z$ photo detectors are preferred for human organic subjects however safety requirements and system performance may demand a different frequency for optimum scan rate. For applications that are not limited, up to 60 $GH_z$ photo detectors are preferred. However, if future technology for higher frequencies are available, the highest available frequency will enable even faster data acquisitions. For inorganic or deceased/perished organic applications, photo detectors up to 40 GHz are preferred. However, if future technology for higher frequencies are available, the highest available frequency is preferred as this will enable even faster data acquisitions.

A user interface 26 comprising a computer with software for data reduction, analysis and 3-D color representation is located outside the enclosure 12. The user interface 26 has a 40 GHz for maximum available inorganic or deceased/perished organic surfaces.

An optic fiber 28 connects scanning head 14 with coupler 20. An optic fiber 30 connects path length variator 18 with the coupler 20. A polarizer 32 is imposed within lead 30 between the variator 18 and the coupler 20.

An optic fiber 34 interconnects the coupler 20 with the photo detector 24. The data communication line 40 connects the photo detector 24 with the user interface 26.

Figure 2:
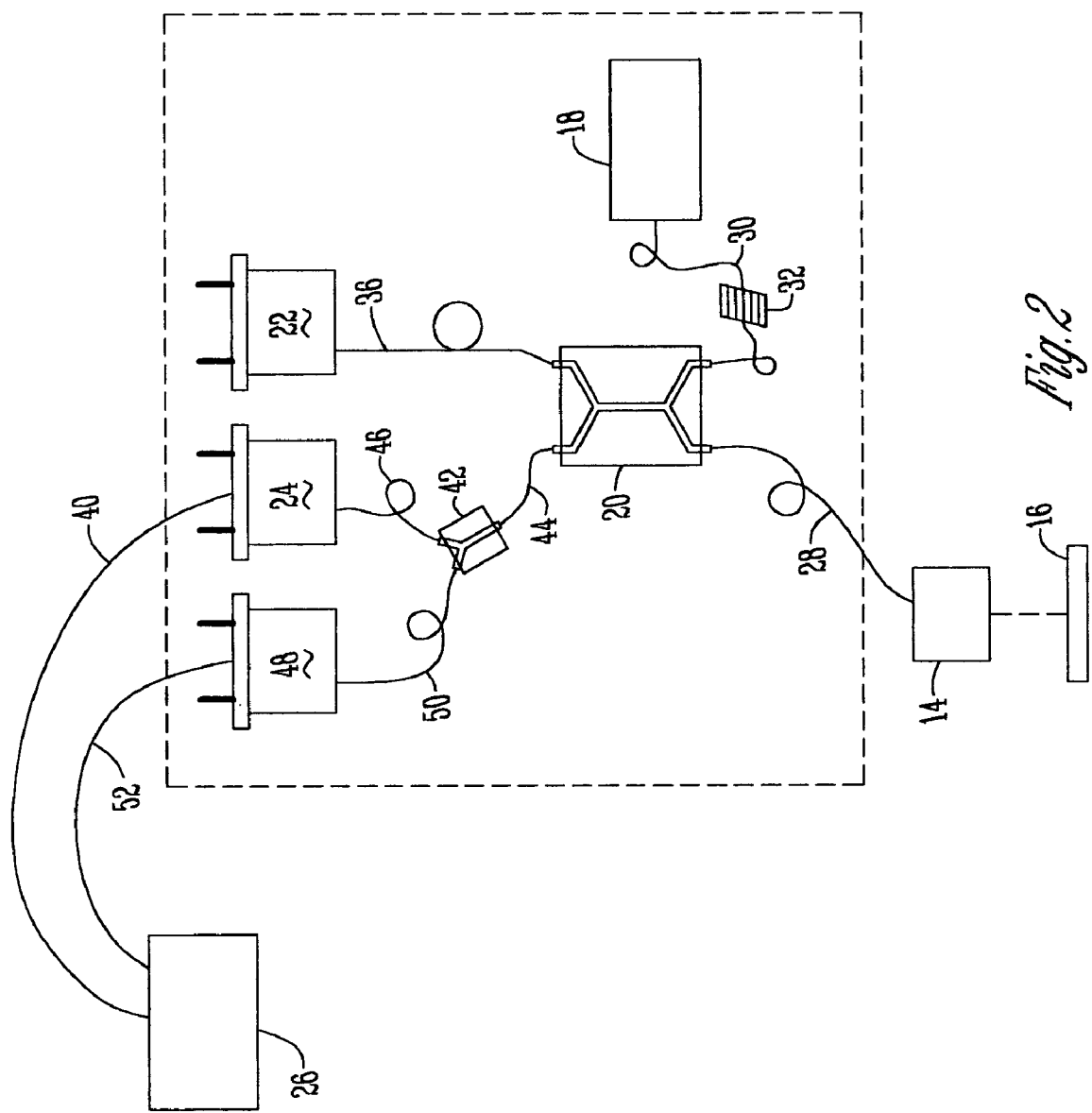
FIG. 2 is a schematic view similar to FIG. 1 but adds a spectrometry feature to that of FIG. 1.

FIG. 2 is similar to FIG. 1 except that FIG. 2 discloses the addition of spectrometry to the system. A coupler 42 is connected to one-way 50/50 coupler 20 by lead 44. A fiber optic 46 connects the coupler 42 to the photo detector 24. A spectrometer detector 48 is located within enclosure 12 and is connected to coupler 42 by fiber optic 50. A fiber optic 52 connects the spectrometer detector 48 with the user interface 26.

Figure 3:
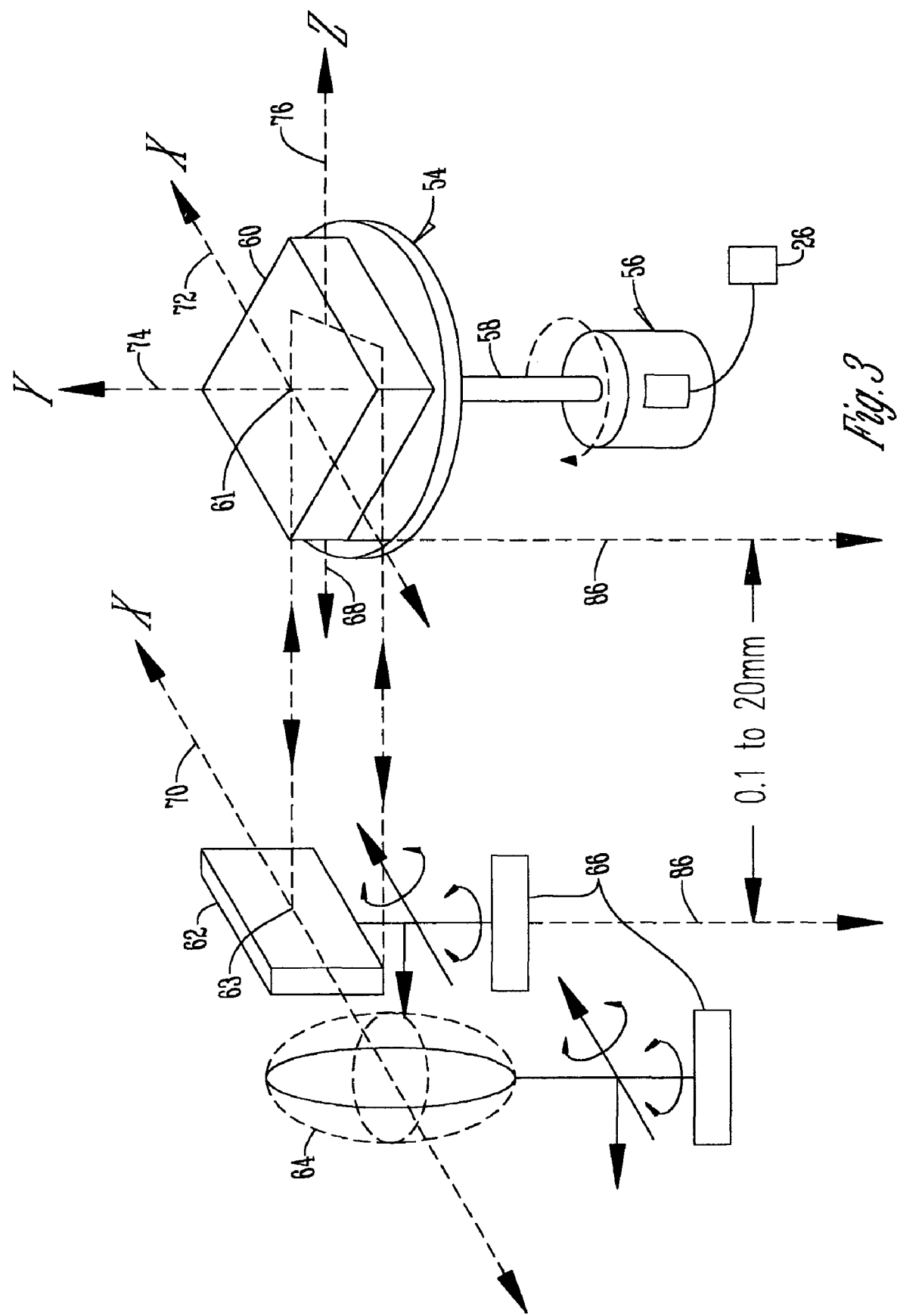
FIG. 3 is a schematic view of the path length variator of this invention.

A schematic view of the path length variator 18 is shown in FIG. 3. A crystal housing 54 is connected to a modular drive system 56 by means of an output shaft 58. Attached to the high speed modular drive system is a rotational/vibration health monitoring system to monitor 3-D vibration, resonance, and imbalance that includes an automated shut-down system with rotation brake. This system is comprised of neural network or comparable technology and is operatively connected to the user interface. Where a gas supply is available, the modular drive system 56 should be comprised of a gas turbine with ball bearings for crystals rotating at design speeds between 80,000 to 500,000 rpms and gas bearings for crystal rotational speeds between 300,000 to 1,500,000 rpms. Where a gas supply is not available, electrical DC motors with ceramic ball bearings can be utilized. A crystal 60 is mounted on crystal housing 54, as will be described in more detail hereafter, and a mirror 62 is located in spaced condition directly opposite from the crystal 60. The mirror 62 should be completely flat without any curvature and should be less than 2 mms in thickness. The mirror should be composed or coated with material having the maximum producible reflection. The center 63 of the mirror is in the same plane and is in direct alignment with the center 61 of crystal 60.

A lens 64 is located adjacent the mirror 62 as are micro-mounting positioning elements 66 which have 3-D plus micro increment elements 66 which have 3-D plus micro increment angular displacement about the X and Y axes positioning capability with less than one micron increments. As shown in FIG. 3, the distance between the center 63 of mirror 62 and the nearest surface of crystal 60 is within the range of 0.1 to 20 mm. The laser beams 68 are exactly parallel to the Z-plane vector described below and exactly parallel to each other in the XZ-plane. The diameter of the focused laser beam 68 on the crystal 60 is 50 to 100 microns. The numeral 70 and 72 represent the X-plane. The numeral 74 designates the Y axis and the numeral 76 designates the Z axis.

Figure 4:
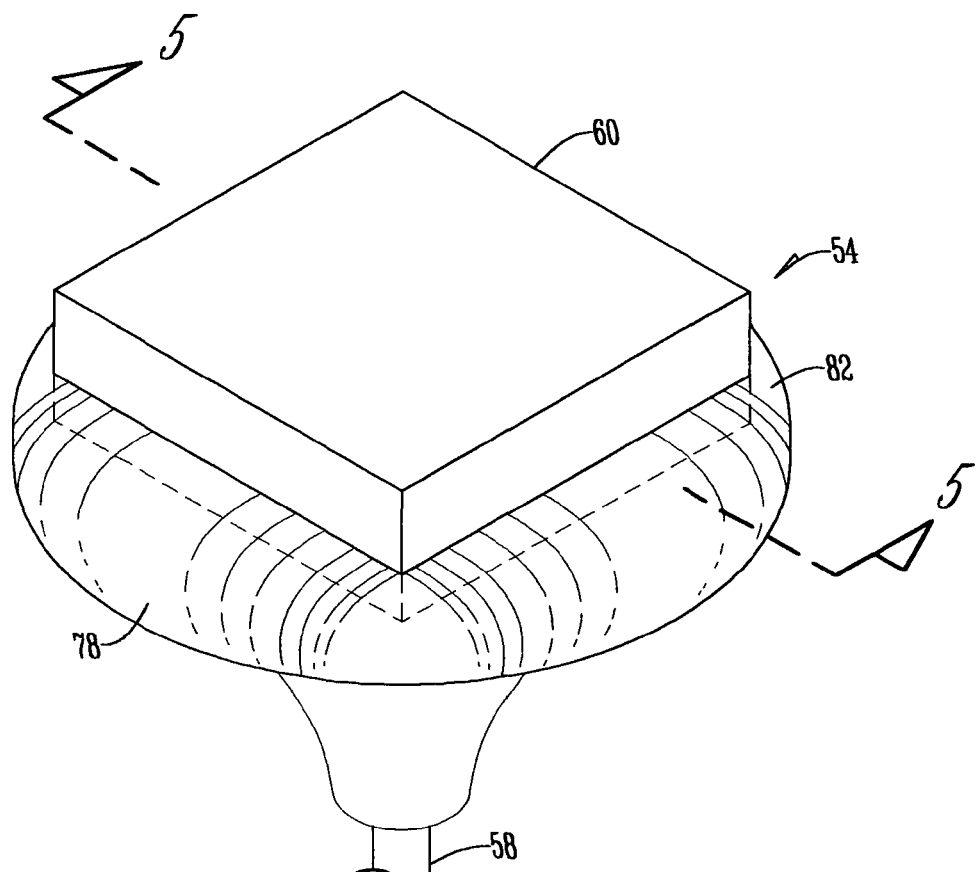
FIG. 4 is a perspective view of the crystal housing of this invention.
Figure 5:
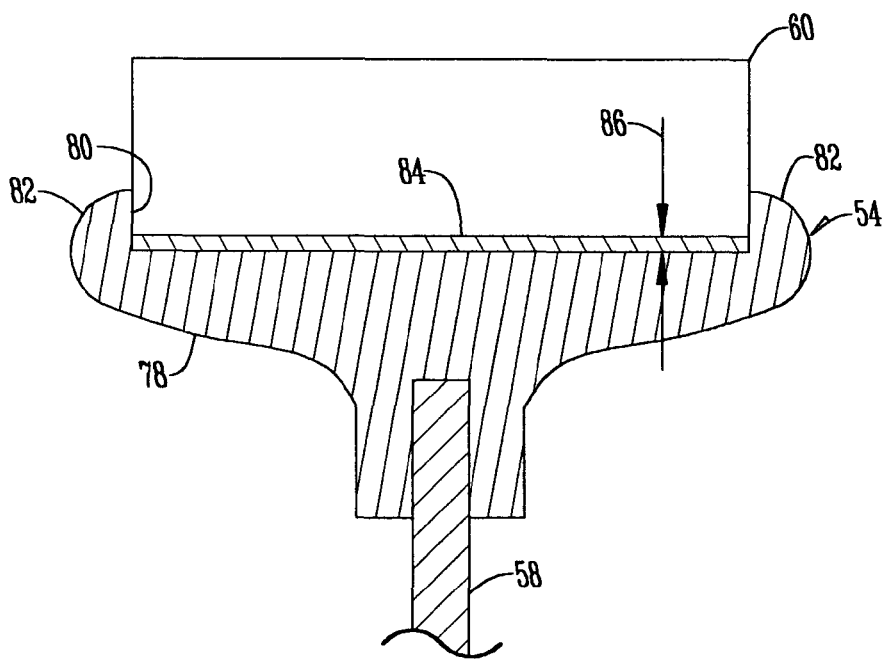
FIG. 5 is a sectional view taken on line 5—5 of FIG. 4.
Figure 6:
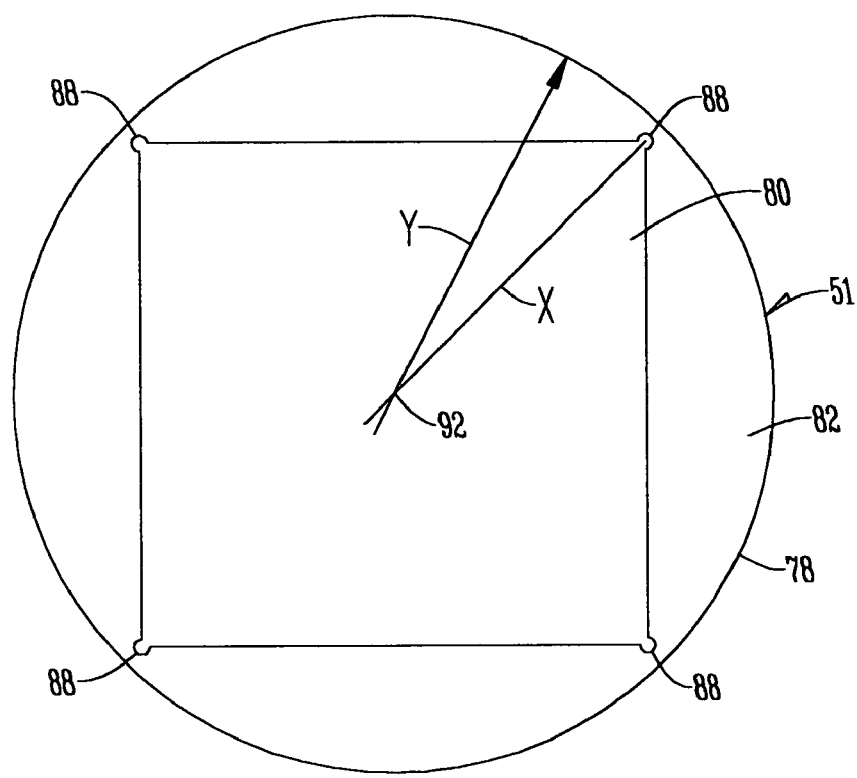
FIG. 6 is a plan view of the crystal housing.

With reference to FIGS. 4 and 5, the crystal housing 54 includes turntable 78 having a rectangular recess 80 therein surrounded by a shoulder 82. A layer of adhesive 84 having a thickness between 0.25 mm and 1.0 mm is located in the bottom of the recess. The layer of adhesive 84 should have homogenous/anisotropic properties to ensure against areas of poor adhesion to minimize any risk of separation and imbalance. Dimension lines 86 indicate the thickness of the layer of adhesive 84 previously discussed. Holes 88 (FIG. 6) are provided in the corners of the square recess 80 for the adhesive of layer 84 to enter to form a column of between 0.3 mm and 1.0 mm diameter in order to not compromise collective crystal, crystal housing, and adhesive system homogeneity. The radius "r" shown in FIG. 6 extending from the center 92 of the housing 54 to the perimeter thereof is equal to the dimension x plus 1 mm to 1.5 mm. The dimension "x" shown in FIG. 6 is equal to ½ of the diagonal distance of the countersunk crystal housing. A mirror 90 is mounted in a similar housing as shown in FIG. 7 wherein the top is generally flat with side edges rounded or contoured in order to minimize aerodynamic drag and weight to achieve high rotational speed.

Figure 7:
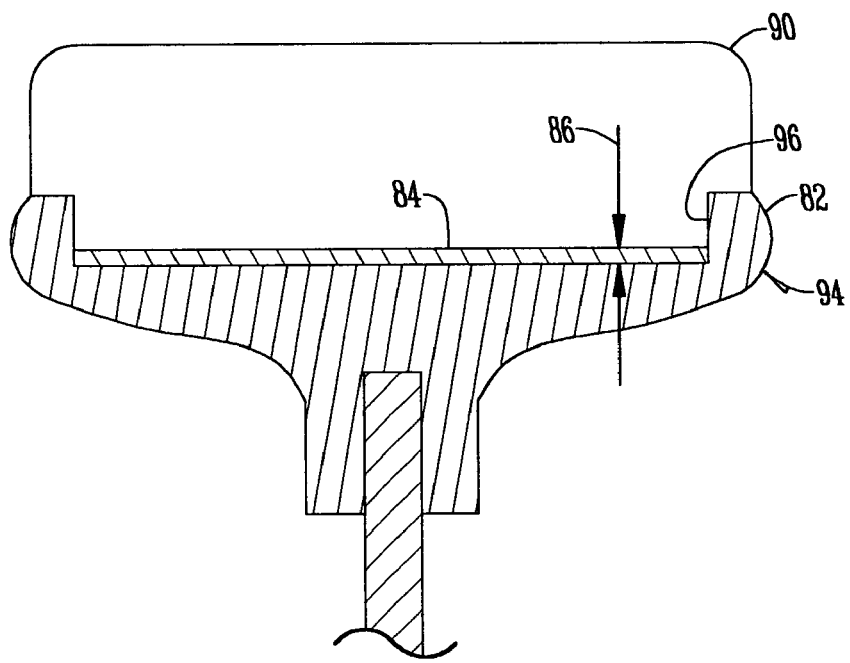
FIG. 7 is a sectional view similar to FIG. 5 but taken through a mirror housing.

With respect to the mirror housing 94 in FIG. 7, the adhesive 84, mirror 90 and mirror housing material, assembly process, rotational balance and optical alignment are designed and optimized to maximize the homogeneity of the collective crystal, adhesive and crystal housing system. This maximizes the strength of the collective system while minimizing weight in order to enable high rotational speeds.

The mirror housing of FIG. 7 should be light and strong to enable high speed rotation and should be comprised of titanium (or material of equivalent or greater Young's Modulus) for rotational speeds of 1,000,000 to 1,500,000 rpms; and can be comprised of aluminum or other material of comparable Young's Modulus for rotational speeds of 500,000 to 1,000,000 rpms. The depth of recess 80 in FIG. 7 should be 10% to 20% of the mirror height. The mirror and mirror housing should be tailored for optimum strength and minimum aerodynamic drag and minimum mass, and can be modified for given applications. The film thickness of the adhesive is 0.25 to 1.0 mms.

Figure 8:
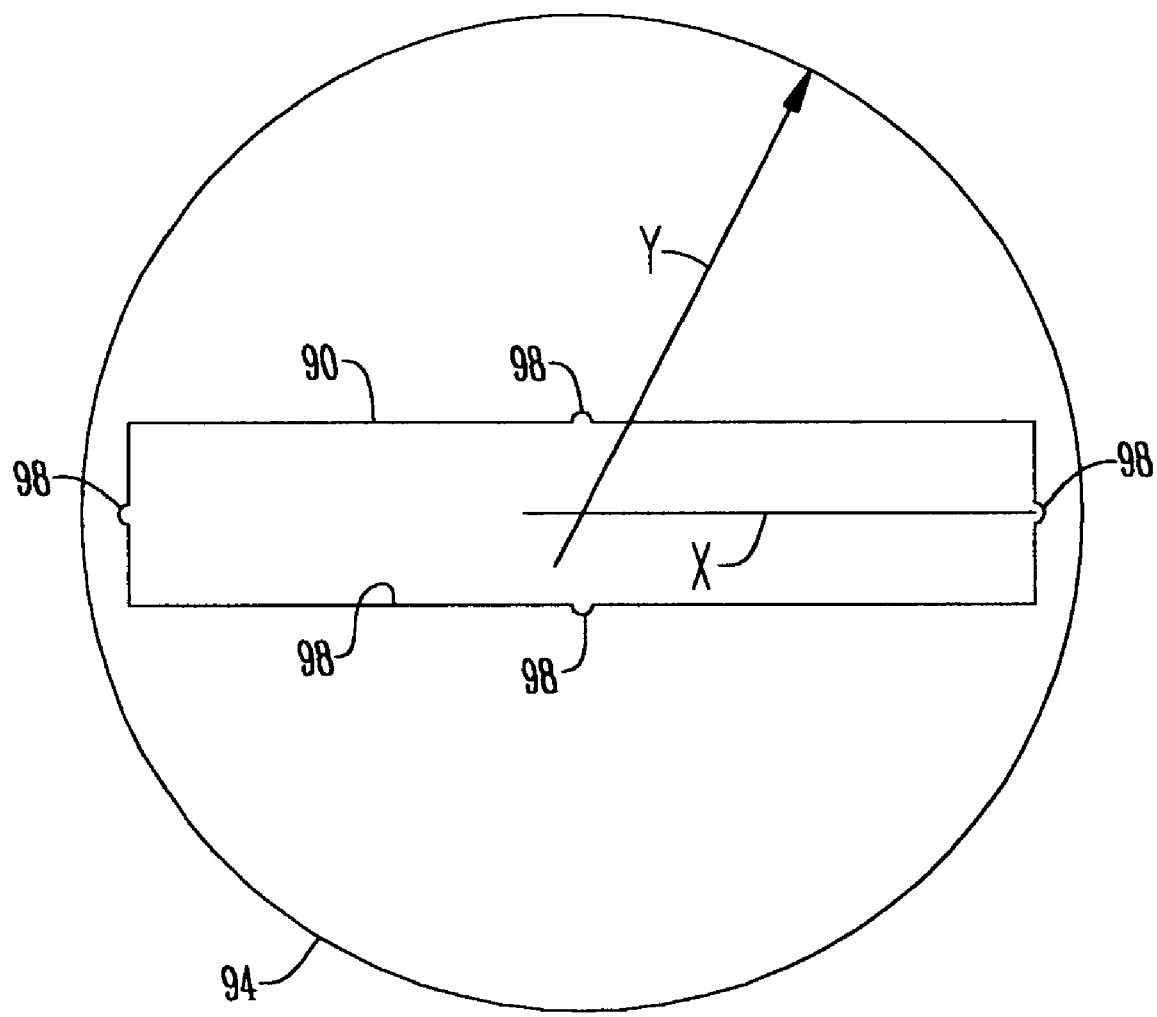
FIG. 8 is a plan view of a mirror housing of FIG. 7.

With reference to FIG. 8, the mirror housing 94 has a cavity 96 with holes 98 to serve essentially as the holes 88 in the crystal housing 54 described above. The thickness of the mirror 90, as discussed heretofore, should be as thin as possible within the limitations that strength and flutter conditions will allow. The radius "r" of the mirror housing is equal to the "x" dimension shown in FIG. 8 plus 0.5 mm to 1.5 mm, wherein x is equal to ½ of the length of the recess 96. Alternatively, it can be considered to design the mirror housing to be rectangular in shape in order to reduce mass if this more favorably enables obtaining a desired rotational speed. In this event, the mirror housing should preferably have its dimensions be between 0.5 mm and 1.5 mm greater than the dimensions of the mirror.

Figure 8A:
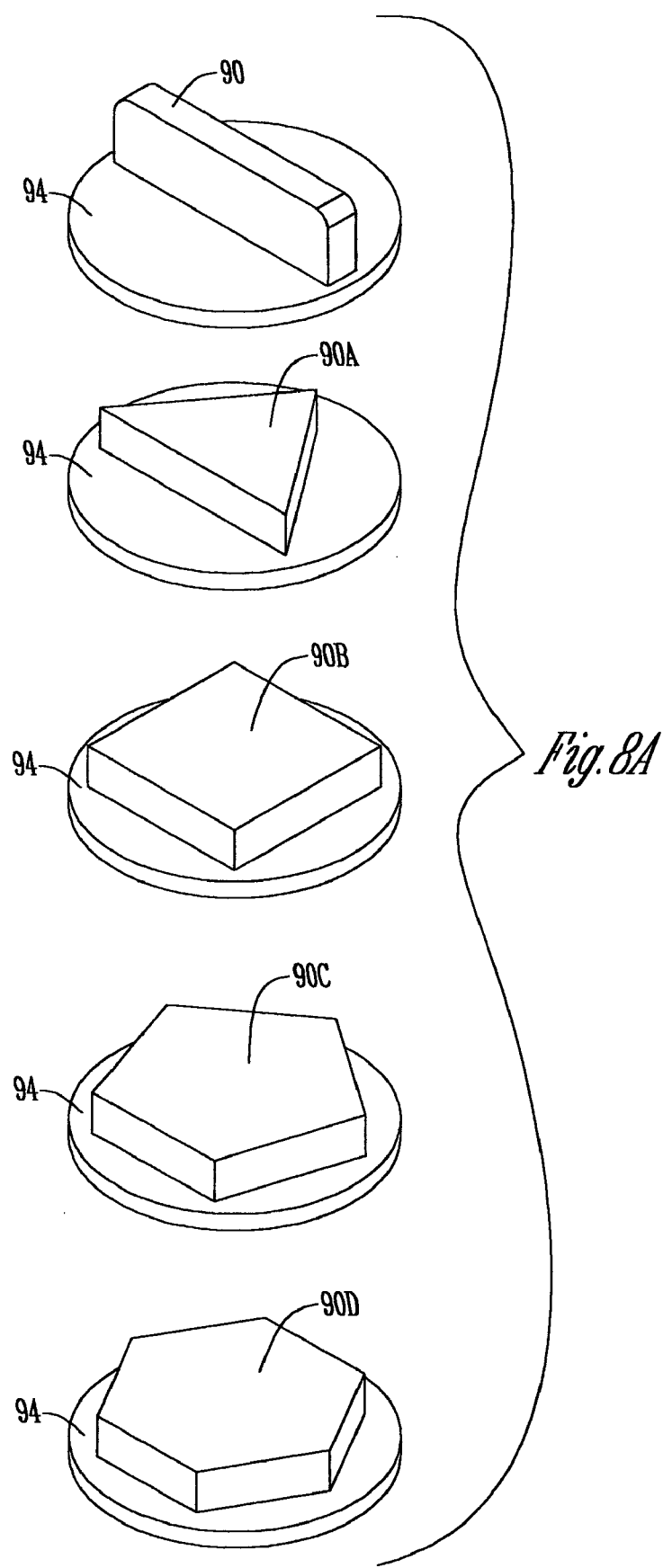
FIG. 8A is a perspective view of alternate mirrors having a different number of sides.

FIG. 8A is a perspective view of mirror 90 with alternate-shaped mirrors 90A, 90B, 90C and 90D showing three, four, five and six sides, respectively, each being mounted on a mirror housing 94. For a given mirror rotational speed capacity, scan rate can also be modulated by using polygon mirrors. The number of sides is limited by the X-Y dimensions of the subject. This flexibility is thus offered to customers as an interchangeable mobile scanning head that can be selected based on requirements dictated by the subject or desired analysis. The requirement for maximum available reflection extends to polygon mirrors as well. The polygon mirrors will have similar mirror housings described previously, in that their materials, external aerodynamic contours, countersink depth, adhesive thickness, and efflux hole dimensions, etc., are optimized based on requirements dictated by the desired rotational speed.

Figure 9:
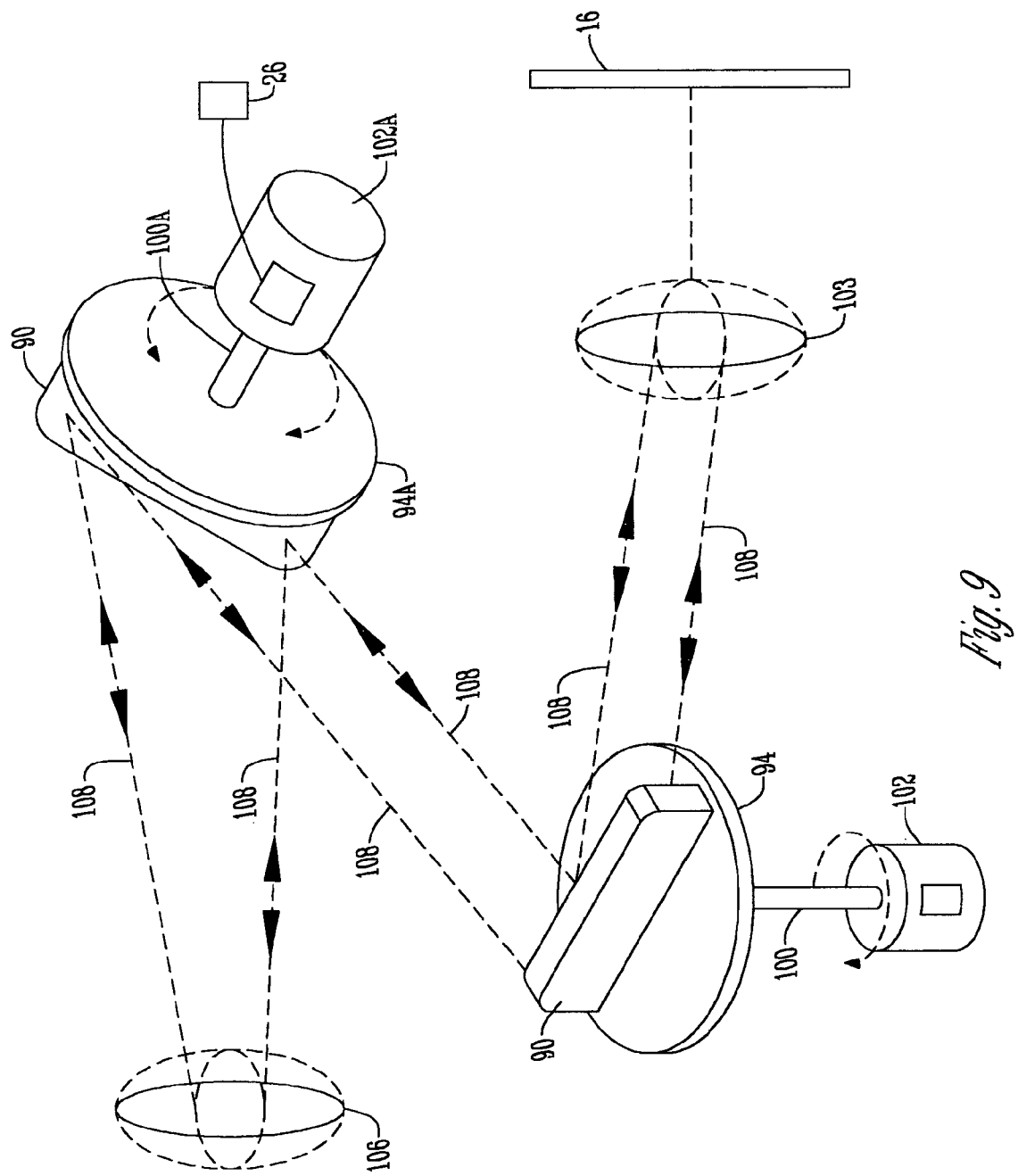
FIG. 9 is a schematic view of the mobile angular scanning head of this invention.

FIG. 9 is a schematic of the mobile angular scanning head 14 of the invention. A shaft 100 interconnects a dual modular drive system 102 with the mirror housing 94. A lens 103 is located in spaced condition to the object 16 being scanned, and in spaced condition to the mirror housing 94.

A second modular drive system 102A is located in spaced condition to the mirror housing 94 and is connected to a second mirror housing 94A by shaft 10A. A lens 106 is located in spaced condition to the mirror 60A on housing 94A. The dotted lines 108 in FIG. 9 designate the path of the sensed light.

Figure 10:
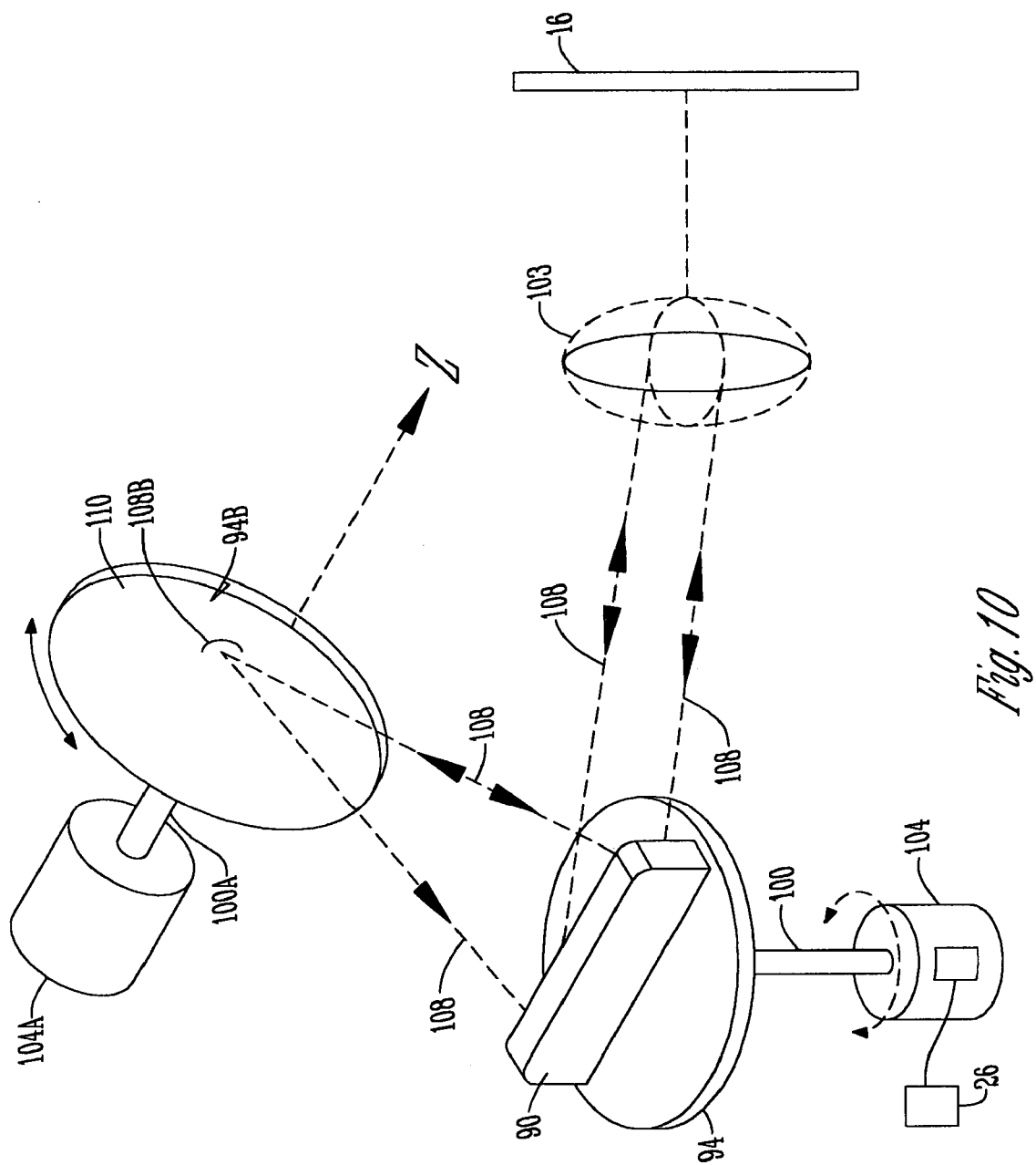
FIG. 10 is a schematic view of an alternate mobile angular scanning head of the invention.

FIG. 10 shows a schematic of an alternate mobile angular scanning head to the schematic drawing in FIG. 9. The arrangement in FIG. 10 is identical to that of FIG. 9 in that scanning head 94B with a curved concave shaped mirror 110 are utilized. The drive system 104A is preferably an oscillatory angular drive system that produces rapid oscillatory angular displacements of the mirror about the rotational axis, but can be modular drive system comparable to modular drive systems 102, 102A, and 104.

Modular drive systems 102, 102A, 104 and 104A have the same operating characteristics as modular drive system 56 in FIG. 3.

Coupling ultra-high speed topography and spectrometry enables the simultaneous 3-dimensional analysis of the surface topography of an object and chemical composition of subjects that are not necessarily stationary. This invention thus enables a product that is capable of detecting the presence, identity and quantity of micro particulates/contaminants on complex organic or inorganic surfaces. Examples include but are not limited to:

Use of structural definition and chemical composition analysis to identify and diagnose state of colorblindness in the retina Forensic detection, identification and positioning of narcotic, chemical, explosive, or propulsive residues on clothing, tissue, or wreckage Detection of chemicals, fertilizers, or poison residue on plants Detection and identification of micro-imperfections including pits, cracks, surface stresses and fissures and chemical homogeneity Topographical and chemical analysis for identification of inclusions and impurities in weldments for assessment of strength uniformity and integrity Validation that fingerprints, retinal scans, or scans of other genetic identifiers are in fact from living or deceased tissue instead of falsifications made from molds or otherwise artificial/illegal simulations created for the purpose of deception Preventative inspection or diagnosis of in-service machinery components, or systems that are in motion, rotating, or stationary which negates the need for costly downtime inspections.

The design is engineered specifically to be adaptable, so the components can be selected before assembly or changed after assembly to enable optimum scan rate, depth and resolution for the subject the customer desires to analyze. In addition, the design can be offered to customers in configurations that only have the topography capability in the event they do not require chemical composition analysis, however the design is engineered to be upgradeable with spectrometry. This affords the customer a very flexible high sustained value device that is not limited to one application and analysis capability.

Thus, it is seen that this invention will accomplish at least all of its stated objectives.

What is claimed is:

1. A 3-dimensional ultra-high speed integrated dual function topography scanning and spectrometer system, whereby ultra-high speed is inclusive of speeds greater than one million rotations per minute comprising, a two-dimensional scanning head operatively associated with a high precision sample positioning arm for scanning an object to be analyzed, the scanning head being operatively associated with a specially balanced ultra-high rotational speed path length variator, the depth or third dimension path length variator being connected by optical fibers to a single mode wavelength coupler, a light source and a photo detectors being operatively connected to the wavelength coupler, a computer with diagnostic software for real-time combination of two dimensional scanning head data and depth or third dimension path length variator data reduction and 3-D data and subject or sample representation connected to both the light source and the photo detector to reveal topographical and chemical composition data of an organic or inorganic object.

2. The ultra-high speed topography scanning and spectrometer system of claim 1 wherein the light source is a photo diode laser.

3. The ultra-high speed topography scanning and spectrometer system of claim 2 wherein the photo diode laser has a capacity of between 633 nm–1550 nm for use in scanning an organic or inorganic object.

4. The ultra-high speed topography scanning and spectrometer system of claim 1 whereby the light source is a laser.

5. The ultra-high speed topography scanning and spectrometer system of claim 1 wherein the light source is a broadband laser.

6. The ultra-high speed topography scanning and spectrometer system of claim 5 wherein the broadband laser has a subject dependent wavelength between 400 and 1700 nm.

7. The ultra-high speed topography scanning and spectrometer system of claim 1 wherein the integrated dual function topography scanning and chemical composition spectrometer system are operatively connected to a scanning system detector and spectrometer-detector by a high-speed optical switch, which is operatively connected to the single mode wavelength coupler with respect to the connection between the wavelength coupler and the single light source.

8. The ultra-high speed topography scanning and spectrometer system of claim 1 wherein the depth or third dimension path length variator is comprised of an aerodynamically optimized crystal housing having an aerodynamically optimized crystal secured thereto with the crystal housing being connected to a source of rotational power comprised of a modular drive system capable of rotating the crystal housing to speeds of 80,000 rpms to 2,000,000 rpms for organic and inorganic subjects.

9. The ultra-high speed topography scanning and spectrometer system of claim 1 wherein the photo detector has a power rating of greater than 10 GHz.

10. The ultra-high speed topography scanning and spectrometer of claim 8 wherein the source of rotational power is an electric motor or gas turbine using ball bearings for operations at speeds between 80,000 and 500,000 rpms.

11. The ultra-high speed topography scanning and spectrometer of claim 8 wherein the source of rotational power is a gas turbine using gas or magnetic bearings for operations at speeds between 300,000 and 2,000,000 rpms.

12. The ultra-high speed topography scanning and spectrometer of claim 8 wherein the path length variator includes a flat fixed mirror spaced opposite from the crystal and having a thickness of less than 2 mm.

13. The ultra-high speed topography scanning and spectrometer of claim 8 wherein the path length variator includes a flat mirror spaced opposite from the crystal and having a thickness of less than 2 mm and a reflective surface comprised of 100% silver.

14. The ultra-high speed topography scanning and spectrometer of claim 12 wherein the nearest position of the crystal and the mirror is between 0.1–20 mm.

15. The ultra-high speed topography scanning and spectrometer of claim 8 wherein the crystal is countersunk a depth a maximum fraction of 0.25 of the crystal thickness in a crystal housing and has a an aerodynamically optimized housing shoulder extending around a perimeter of the crystal.

16. The ultra-high speed topography scanning and spectrometer of claim 15 wherein the crystal is received with a cavity within the housing surrounded by the housing shoulder; the cavity having a flat bottom, and a layer of slow cure, high tensile strength adhesive positioned between the bottom and a bottom surface of the crystal.

17. The ultra-high speed topography scanning and spectrometer of claim 8 wherein the crystal has a 3-dimensional wherby the number of reflective faces subject dependent.

18. The ultra-high speed topography scanning and spectrometer of claim 8 wherein the housing is circular in a horizontal plane, wherein the contour shape is aerodynamically and mass optimized for ultra high-speed.

19. The ultra-high speed topography scanning and spectrometer of claim 8 wherein an x plane is defined as a horizontal plane extending through the crystal and the mirror; and a y axis extends vertically through a vertical center axis of the crystal, and a z-axis extends from the center of the crystal to the mirror in the x-plane, and the laser beams are directed to pass exactly to a parallel z-plane vector and exactly parallel to each other in an x-z plane.

20. The ultra-high speed topography scanning and spectrometer of claim 1 wherein the scanning head comprises first and second crystals counter-sunk into crystal housings disposed on first and second axes, respectively, which are substantially perpendicular to each other which enables two-dimensional associated information, the crystals being each operatively connected to shafts on their respective axes by modular drive systems capable of speeds of between 80,000 and 2,000,000 rpms.

21. The scanning head of claim 20 wherein the length of the first and second crystals are substantially equal to the maximum breadth of the object being scanned.

22. The ultra-high speed topography scanning and spectrometer of claim 1 wherein the path length variator and scanning head are comprised of crystal housings having a crystal secured thereto with the crystal housing being connected to a source of rotational power about an axis of rotation, and the light source is a laser beam having a path of projection, and the axis of rotation of the crystal and each face of the crystal is always perpendicular to the path of projection of the laser.

23. The systems of claim 22 wherein the source of rotational power for the crystals are comprised of a modular drive system capable of rotating the crystal housing to speeds of 300,000 rpms to 2,000,000 rpms.

24. The scanning systems of claim 22 wherein the laser is a broadband laser with a capacity of up to 1500 nm.

25. The ultra-high speed topography scanning and spectrometer system of claim 8 wherein the depth or third dimension path length variator is comprised of a weight optimized crystal housing having a crystal secured thereto with the crystal housing being connected to a source of rotational power comprised of a modular drive system capable of rotating the crystal housing to speeds of 80,000 rpms to 2,000,000 rpms for organic and inorganic subjects.

26. The ultra-high speed topography scanning and spectrometer scanning system of claim 16 wherein the crystal is received with a cavity which contains a plurality of holes of maximum radius 0.1 mm equivalent to the number of crystal faces that are drilled in the corners or sidewalls of the cavity to permit glue egress during the process of precisely setting the crystal with respect to the light source prior to glue cure.

27. The ultra-high speed topography scanning and spectrometer scanning system of claim 20 wherein the scanning head comprises first and or second optical rotating mirrors disposed on first and second axes, respectively, which are substantially perpendicular to each other which enables two-dimensional associated information, the rotating mirrors being each operatively connected to shafts on their respective axes by modular drive systems whose maximum rotational speed is defined by the resonant frequency of the rotating mirrors which enables even higher sampling rates.

28. The modular drive systems of claim 8 wherein the source of rotational power for the crystals are is comprised of helium gas to enable the maximum rotational speed.

29. The modular drive systems of claim 8 wherein the counter-sunk crystals and crystal housing can be wholly contained in an outer transparent housing of internal vacuum pressure to eliminate air friction.

30. The complete system of claim 1 is housed in a portable transport system of sufficient strength for ballistic containment.

* * * * *